United States Patent
Herrmann et al.

(10) Patent No.: US 11,607,457 B2
(45) Date of Patent: Mar. 21, 2023

(54) ANTI-CANCER PHOSPHOROTHIOATE-COUPLED PEPTIDE CONJUGATES AND METHODS OF USING THE SAME

(71) Applicants: CITY OF HOPE, Duarte, CA (US); Sorrento Therapeutics, Inc., San Diego, CA (US)

(72) Inventors: Andreas Herrmann, Del Mar, CA (US); Hua Yu, Glendora, CA (US); Yanwen Fu, San Diego, CA (US)

(73) Assignees: CITY OF HOPE, Duarte, CA (US); SORRENTO THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/630,347

(22) PCT Filed: Jul. 13, 2018

(86) PCT No.: PCT/US2018/042179
§ 371 (c)(1),
(2) Date: Jan. 10, 2020

(87) PCT Pub. No.: WO2019/014650
PCT Pub. Date: Jan. 17, 2019

(65) Prior Publication Data
US 2021/0154305 A1    May 27, 2021

Related U.S. Application Data

(60) Provisional application No. 62/532,149, filed on Jul. 13, 2017.

(51) Int. Cl.
*A61K 48/00* (2006.01)
*C07H 21/04* (2006.01)
(Continued)

(52) U.S. Cl.
CPC ............ *A61K 47/549* (2017.08); *A61P 35/00* (2018.01)

(58) Field of Classification Search
CPC ...... C12N 2310/315; C12N 2310/3513; C12N 15/11; C12N 15/113; C12N 2320/30; C07K 16/40; A61K 47/549
See application file for complete search history.

(56) References Cited

U.S. PATENT DOCUMENTS 10,967,070 B2 * 4/2021 Herrmann .............. C07K 16/40
2005/0175606 A1    8/2005 Huang et al.
(Continued)

FOREIGN PATENT DOCUMENTS

WO    WO-9320238 A2 * 10/1993 ......... G01N 33/5011
WO    WO-2015031837 A1 * 3/2015 ................ A61P 9/00
(Continued)

OTHER PUBLICATIONS

Amino Acid Molecular Weights downloaded from https://www.promega.com/resources/tools/amino-acid-chart-amino-acid-structure/ on Jan. 11, 2022.*
(Continued)

*Primary Examiner* — Terra C Gibbs
(74) *Attorney, Agent, or Firm* — Mintz, Levin, Cohn, Ferris, Glovsky and Popeo, P.C.

(57) ABSTRACT

Provided herein are, inter alia, nucleic acid-peptide conjugates including a non-cell penetrating protein (e.g., an Hdm2 targeting peptide) attached at its C-terminus to a phosphorothioate nucleic acid. Attachment of the phosphorothioate nucleic acid to the non-cell penetrating protein conveys stability to and allows for efficient intracellular delivery of the non-cell penetrating peptide. The nucleic acid-peptide
(Continued)

---

Peptide/DNA #1

N-terminus                                           C-terminus    5'-                                                              -3'
Ac-Leu-Thr-Phe-Aib-Glu-Tyr-Trp-Aib-Gln-Leu-Aib-Ser-Ala-NH2-linker-T*C*C*A*T*G*A*G*C*T*T*C*C*T*G*A*T*G*C*T

Peptide/DNA #2

N-terminus                                           C-terminus    5'-                                                              -3'
Ac-Leu-Thr-Phe-Aib-Glu-Tyr-Trp-Aib-Gln-Leu-Aib-Ser-Ala-NH2-linker-TCCATGAGCTTCCTGATGCT Aib: aminoisobutyric acid conjugates provided herein including embodiments thereof are useful, inter alia, for the treatment of cancer.

11 Claims, 6 Drawing Sheets

Specification includes a Sequence Listing.

(51) Int. Cl.
*A61K 47/54* (2017.01)
*A61P 35/00* (2006.01)

(56) References Cited

U.S. PATENT DOCUMENTS

| | | |
|---|---|---|
| 2007/0269435 A1 | 11/2007 | Gillies et al. |
| 2010/0113747 A1 | 5/2010 | Kjaergaard et al. |
| 2012/0165268 A1 | 6/2012 | Lin et al. |
| 2013/0266570 A1 | 10/2013 | Weisbart et al. |
| 2013/0274205 A1 | 10/2013 | Guerlavais et al. |
| 2014/0030726 A1 | 1/2014 | Mayo |
| 2015/0183825 A1 | 7/2015 | Guerlavais et al. |
| 2017/0008970 A1 | 1/2017 | Babcook et al. |

FOREIGN PATENT DOCUMENTS

| | | |
|---|---|---|
| WO | WO-2017/024239 A1 | 2/2017 |
| WO | WO-2017/066441 A1 | 4/2017 |

OTHER PUBLICATIONS

International Search Report dated Oct. 2, 2018, for PCT Application No. PCT/US2018/042179, filed Jul. 13, 2018, 4 pages.
Written Opinion dated Oct. 2, 2018, for PCT Application No. PCT/US2018/042179, filed Jul. 13, 2018, 8 pages.

* cited by examiner

Peptide/DNA #1

N-terminus                                          C-terminus   5'-                             -3'

Ac-Leu-Thr-Phe-Aib-Glu-Tyr-Trp-Aib-Gln-Leu-Aib-Ser-Ala-NH2-linker-T*C*C*A*T*G*A*G*C*T*T*C*C*T*G*A*T*G*C*T

Peptide/DNA #2

N-terminus                                          C-terminus   5'-                -3'

Ac-Leu-Thr-Phe-Aib-Glu-Tyr-Trp-Aib-Gln-Leu-Aib-Ser-Ala-NH2-linker-TCCATGAGCTTCCTGATGCT Aib: aminoisobutyric acid

***p-value < 0.0001

SEQUENCE LISTING

<160> NUMBER OF SEQ ID NOS: 4

<210> SEQ ID NO 1
<211> LENGTH: 393
<212> TYPE: PRT

<213> ORGANISM: Artificial sequence
<220> FEATURE:
<223> OTHER INFORMATION: Synthetic polypeptide

<400> SEQUENCE: 1

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
```

<210> SEQ ID NO 2
<211> LENGTH: 491
<212> TYPE: PRT
<213> ORGANISM: Artificial sequence
<220> FEATURE:
<223> OTHER INFORMATION: Synthetic polypeptide

<400> SEQUENCE: 2

```
Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
        195                 200                 205

Arg Ser Ser Ser Ser Glu Ser Thr Gly Thr Pro Ser Asn Pro Asp Leu
    210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Glu Ser Leu Asp Ser
                245                 250                 255

Glu Asp Tyr Ser Leu Ser Glu Glu Gly Gln Glu Leu Ser Asp Glu Asp
            260                 265                 270

Asp Glu Val Tyr Gln Val Thr Val Tyr Gln Ala Gly Glu Ser Asp Thr
        275                 280                 285

Asp Ser Phe Glu Glu Asp Pro Glu Ile Ser Leu Ala Asp Tyr Trp Lys
    290                 295                 300

Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
                325                 330                 335

Asp Lys Gly Glu Ile Ser Glu Lys Ala Lys Leu Glu Asn Ser Thr Gln
            340                 345                 350

Ala Glu Glu Gly Phe Asp Val Pro Asp Cys Lys Lys Thr Ile Val Asn
```

```
                355                 360                 365
Asp Ser Arg Glu Ser Cys Val Glu Glu Asn Asp Asp Lys Ile Thr Gln
    370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
                405                 410                 415

Glu Glu Thr Gln Asp Lys Glu Gly Ser Val Glu Ser Ser Leu Pro Leu
            420                 425                 430

Asn Ala Ile Glu Pro Cys Val Ile Cys Gln Gly Arg Pro Lys Asn Gly
            435                 440                 445

Cys Ile Val His Gly Lys Thr Gly His Leu Met Ala Cys Phe Thr Cys
        450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
                485                 490

<210> SEQ ID NO 3
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (11)..(11)
<223> OTHER INFORMATION: Aib

<400> SEQUENCE: 3

Leu Thr Phe Xaa Glu Tyr Trp Xaa Gln Leu Xaa Ser Ala
1               5                   10

<210> SEQ ID NO 4
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 4
tccatgagct tcctgatgct                                           20
```

ANTI-CANCER PHOSPHOROTHIOATE-COUPLED PEPTIDE CONJUGATES AND METHODS OF USING THE SAME

CROSS REFERENCE TO RELATED APPLICATIONS

This application is a national stage filing under U.S.C. 371 of international application PCT/US18/42179, filed Jul. 13, 2018, which claims priority to U.S. Provisional Application No. 62/532,149, filed Jul. 13, 2017, which are hereby incorporated by reference in their entirety and for all purposes.

STATEMENT AS TO RIGHTS TO INVENTIONS MADE UNDER FEDERALLY SPONSORED RESEARCH AND DEVELOPMENT

This invention was made using support under Grant Number CA122976 awarded by the National Institutes of Health. The government has certain rights to this invention.

REFERENCE TO A SEQUENCE LISTING, A TABLE OR A COMPUTER PROGRAM LISTING APPENDIX SUBMITTED AS AN ASCII TEXT FILE

The Sequence Listing written in file 048440 664001WO_ST25.TXT, created Jul. 13, 2018, 8,729 bytes, machine format IBM-PC, MS Windows operating system, is hereby incorporated by reference.

BACKGROUND OF THE INVENTION

Tumor suppressor protein p53 plays an important role in preventing cells from becoming cancerous. Inactivation of p53 through mutation, deletion, or inhibitory proteins is the most common defect in human cancers. Inhibitory proteins such as Hdm2, also known as Mdm2, can interact with p53 intracellularly to cause ubiquitination and subsequent degradation of the p53 protein. In certain cancers, Hdm2 is over-expressed leading to a decrease in p53 protein in cancer tissue and a loss of tumor suppression. Thus, interrupting the intracellular interaction of Hdm2 with p53 is considered a promising point of therapeutic intervention in cancer.

Targeting intracellular molecules for therapeutic purposes is particularly challenging due to the need for the targeting molecule to both penetrate the cell membrane and maintain biostability in a physiological environment. Provided herein are compositions and methods including targeting peptides conjugated to phophorothioate nucleic acids at their C-terminus which exhibit surprising biostability and can be delivered intracellularly with high efficiency. The phosphorothioate nucleic acid-peptide conjugates provided herein are, inter alia, useful for the treatment of cancer.

BRIEF SUMMARY OF THE INVENTION

In an aspect is provided a nucleic acid-peptide conjugate including: (i) a non-cell penetrating peptide; (ii) a phosphorothioate nucleic acid; and (iii) a chemical linker attaching the phosphorothioate nucleic acid to the C-terminus of the non-cell penetrating peptide; wherein the phosphorothioate nucleic acid enhances intracellular delivery of the non-cell penetrating peptide.

In an aspect is provided a cell including the peptide conjugate provided herein including embodiments thereof.

In an aspect is provided a pharmaceutical composition including the peptide conjugate as provided herein including embodiments thereof and a pharmaceutically acceptable carrier.

In an aspect is provided a method of treating cancer in a subject in need thereof. The method includes administering to the subject a therapeutically effective amount of a cell penetrating peptide conjugate as provided herein including embodiments thereof, thereby treating the cancer in the subject.

In an aspect is provided a method of inhibiting degradation of p53 in a cancer cell, the method including contacting a cancer cell with an effective amount of a cell penetrating peptide conjugate as provided herein including embodiments thereof, thereby inhibiting degradation of p53 in the cancer cell.

In an aspect is provided a method of inhibiting Hdm2 phosphorylation in a cell, the method including contacting a cell with an effective amount of a cell penetrating peptide conjugate as provided herein including embodiments thereof, thereby inhibiting Hdm2 phosphorylation in the cell.

In an aspect is provided a method of delivering a non-cell penetrating peptide into a cell, the method including contacting a cell with a cell penetrating peptide conjugate as provided herein including embodiments thereof, thereby delivering the non-cell penetrating peptide into the cell.

BRIEF DESCRIPTION OF THE DRAWINGS

FIG. 2A. Human HCT116 colon cancer cells were incubated for 4 hrs with peptides as indicated and cellular uptake was assessed by flow cytometry. FIG. 2B. Cellular internalization of PS-modified p53 (Mdm2 targeting peptide, peptide of SEQ ID NO:3) targeting peptide but not PO-modified p53 targeting peptide (Mdm2 targeting peptide, peptide of SEQ ID NO:3) by human HCT116 colon cancer cells after 4 hrs of incubation with 10 µg/ml peptide was shown by confocal microscopy. Scale, 20 µm.

FIG. 3A. Human HCT116 colon cancer cells were engrafted in athymic nude mice and tumor were treated every other day with 20 mg and growth kinetics were assessed. SD shown, T-test: *) P<0.05. FIG. 3B. Tumor homogenates isolated from tumors treated as described in FIG. 3A were subjected to electrophoretic protein separation by SDS-PAGE and decreased serine-phosphorylation of Mdm2 was assessed by Western blot detection. FIG. 3C.

Figure 3A:
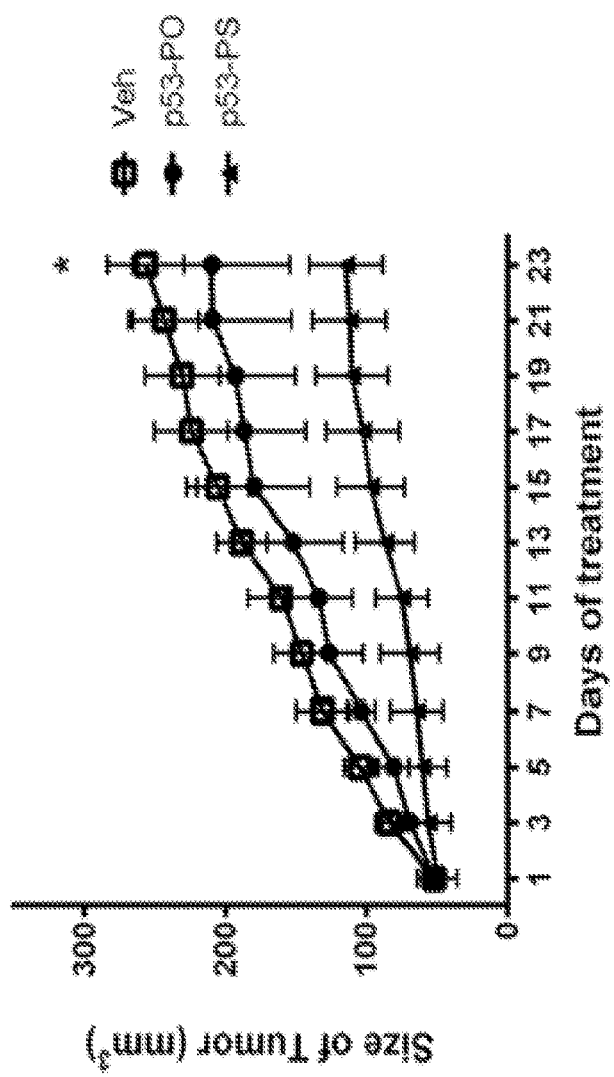
FIGS. 3A-3C: Targeting p53 with PS-p53 modified-peptide (Mdm2 targeting peptide, peptide of SEQ ID NO:3) reduces tumor growth.

mRNA was isolated from tumor treated as described in FIG. 3A and gene expression was assessed by RT-PCR. SD shown.

Figure 4A:
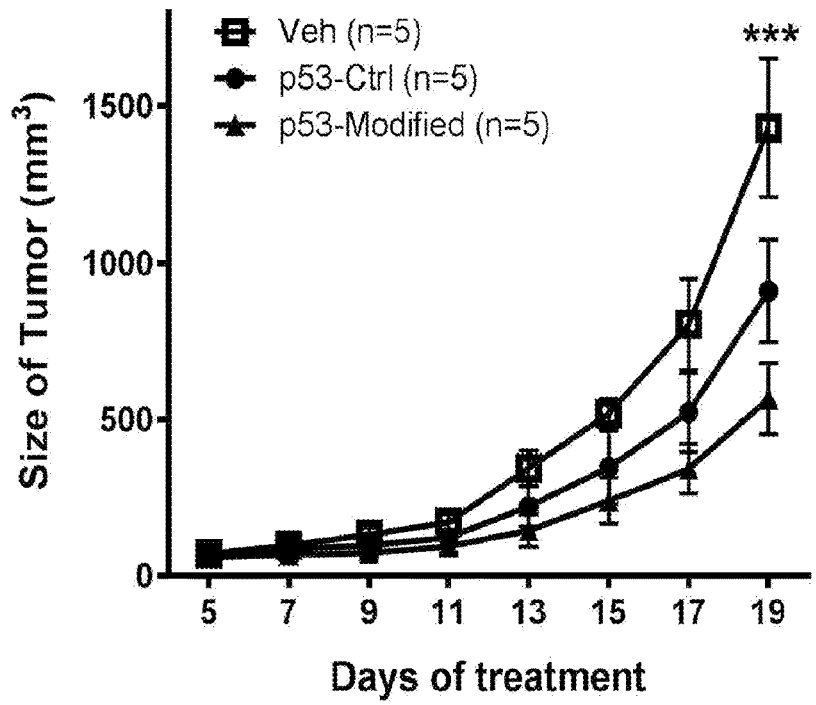
Figure 4B:
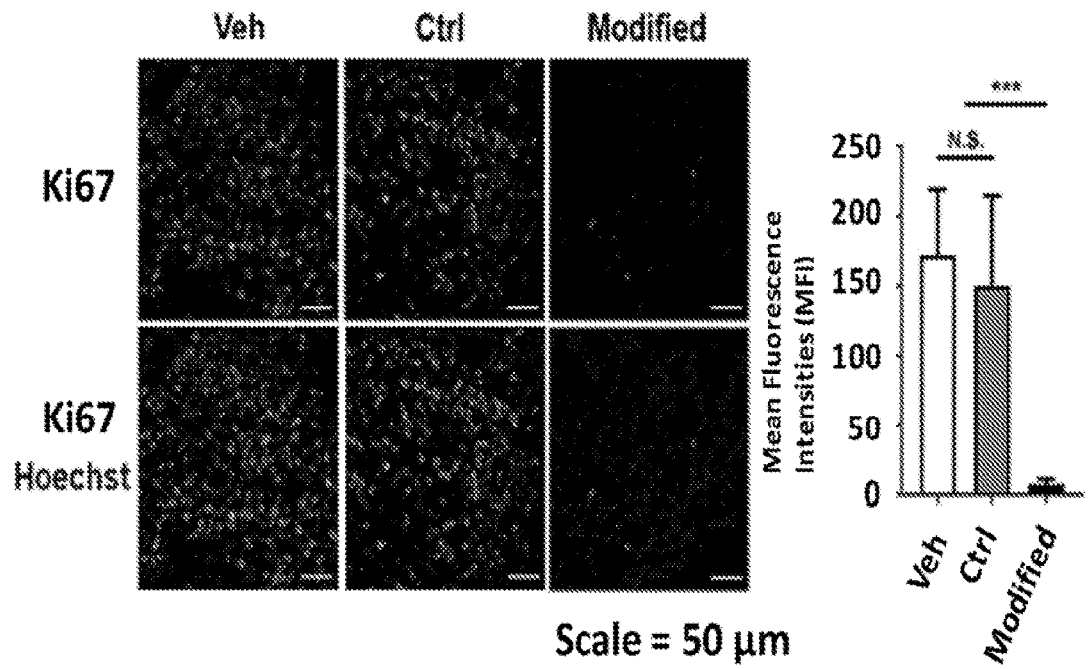
Figure 4C:
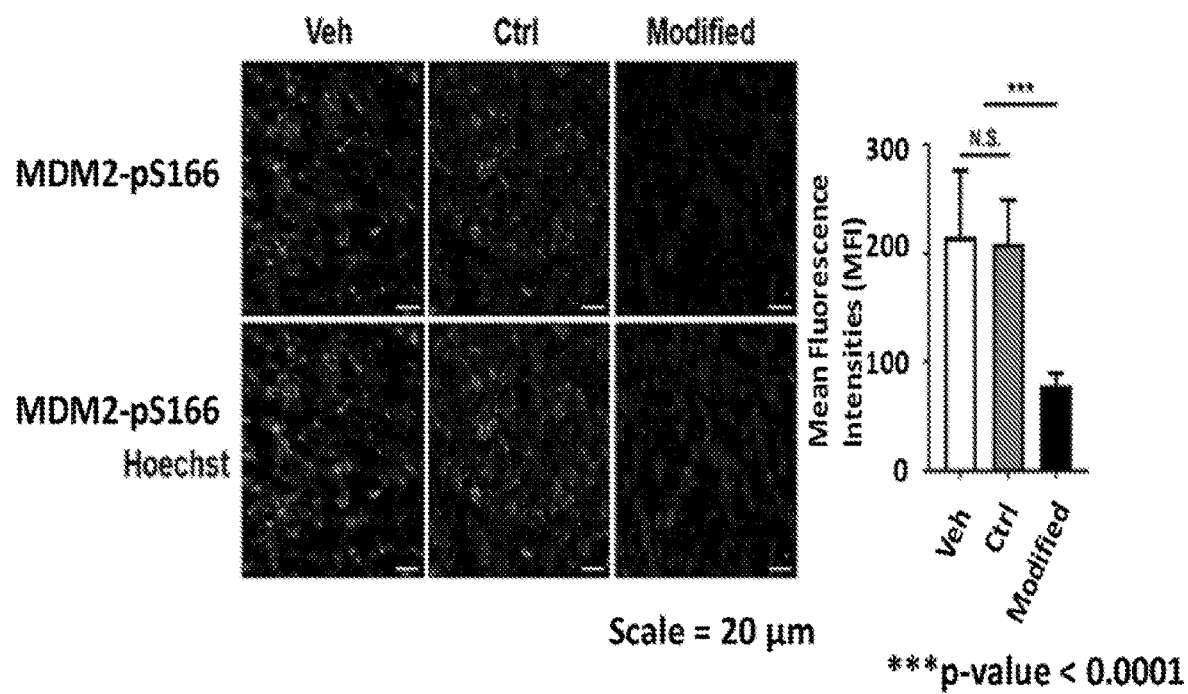

FIGS. 4A-4C: Anti-tumor efficacy of p53 modified peptide (Mdm2 targeting peptide, peptide of SEQ ID NO:3). FIG. 4A. Treating mice locally bearing human multiple myeloma tumors with peptides as indicated resulted in significantly delayed tumor growth kinetics upon administration of p53 modified peptide (Mdm2 targeting peptide, peptide of SEQ ID NO:3). Tumor tissue sections dissected from tumors were stained for (FIG. 4B) Ki67+proliferative activity and (FIG. 4C) Mdm2 serine phosphorylation critical for interaction with p53. Both, Ki67 and pS-Mdm2 expression were significantly reduced upon treatment with p53 modified peptide (Mdm2 targeting peptide, peptide of SEQ ID NO:3) in vivo.

Figure 5:
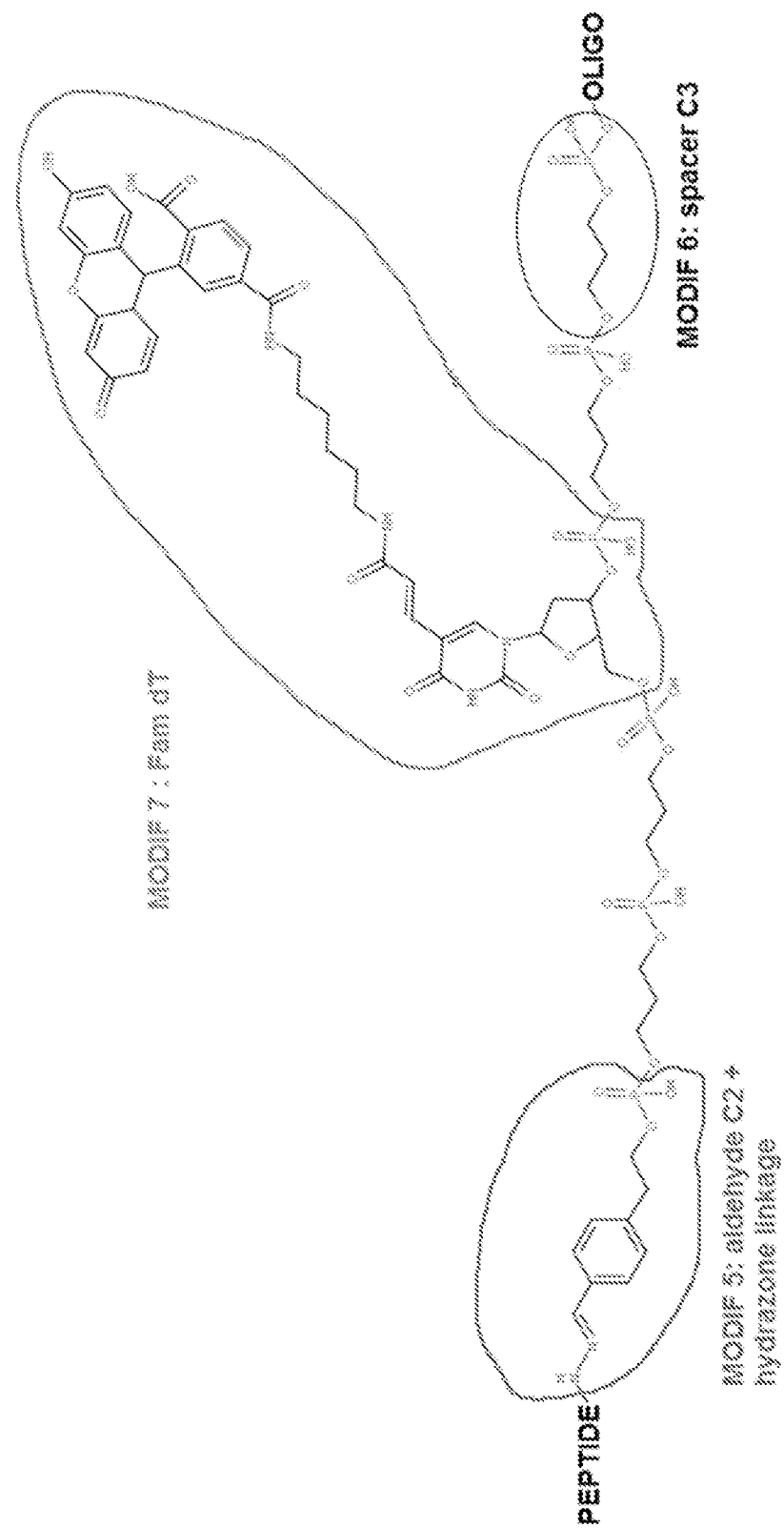

FIG. 5: Scheme of modified peptide sequences (peptide) connected via a Linker (aldehyde C2+hydrazine linkage) and spacers (C3) including a fluorescent tag (Fam dT) to a phosphorothioate ssDNA (oligo).

DETAILED DESCRIPTION OF THE INVENTION

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Cycloalkyl and heterocycloalkyl are non-aromatic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section or Drawings.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R"", —CN, —NO$_2$, monophosphate (or derivatives thereof), diphosphate (or derivatives thereof), triphosphate (or derivatives thereof), in a number ranging from zero to (2m'+1), where m' is the total number of carbon atoms in such radical. R, R', R", R''', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R"", —CN, —NO$_2$, —R', —N$_3$, —CH(Ph)$_2$, fluoro(C$_1$-C$_4$)alkoxy, and fluoro(C$_1$-C$_4$)alkyl, monophosphate (or derivatives thereof), diphosphate (or derivatives thereof), triphosphate (or derivatives thereof), in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

When a compound of the invention includes more than one R group, for example, each of the R groups is independently selected as are each R', R", R''', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and
(B) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and
  (ii) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and
    (b) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), and triphosphate (or derivatives thereof).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The symbol "⌇" denotes the point of attachment of a chemical moiety to the remainder of a molecule or chemical formula.

A "chemical linker" or "linker" as provided herein is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties can be chemically different.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted C$_1$-C$_{20}$ alkyl, or unsubstituted 2 to 20 membered heteroalkyl," the group may contain one or more unsubstituted C$_1$-C$_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus, a Roman alphabetic symbol may be used to distinguish each appearance of that particular R group. For example, where multiple R$^1$ substituents are present, each R$^1$ substituent may be distinguished as R$^{1A}$, R$^{1B}$, R$^{1C}$, R$^{1D}$, etc., wherein each of R$^{1A}$, R$^{1B}$, R$^{1C}$, R$^{1D}$, etc. is defined within the scope of the definition of R$^1$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different from the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

The term "phosphorothioate nucleic acid" refers to a nucleic acid in which one or more internucleotide linkages are through a phosphorothioate moiety (thiophosphate) moiety. The phosphorothioate moiety may be a monothiophosphate ($-P(O)_3(S)^{3-}-$) or a dithiophosphate ($-P(O)_2(S)_2^{3-}-$). In embodiments of all the aspects provided herein, the phosphorothioate moiety is a monothiophosphate ($-P(O)_3(S)^{3-}-$). That is, in embodiments of all the aspects provided herein, the phosphorothioate nucleic acid is a monothiophosphate nucleic acid. In embodiments, one or more of the nucleosides of a phosphorothioate nucleic acid are linked through a phosphorothioate moiety (e.g. monothiophosphate) moiety, and the remaining nucleosides are linked through a phosphodiester moiety ($-P(O)_4^{3-}-$). In embodiments, one or more of the nucleosides of a phosphorothioate nucleic acid are linked through a phosphorothioate moiety (e.g. monothiophosphate) moiety, and the remaining nucleosides are linked through a methylphosphonate linkage. In embodiments, all the nucleosides of a phosphorothioate nucleic acid are linked through a phosphorothioate moiety (e.g. a monothiophosphate) moiety.

Phosphorothioate oligonucleotides (phosphorothioate nucleic acids) are typically from about 5, 6, 7, 8, 9, 10, 12, 15, 25, 30, 40, 50 or more nucleotides in length, up to about 100 nucleotides in length. Phosphorothioate nucleic acids may also be longer in lengths, e.g., 200, 300, 500, 1000, 2000, 3000, 5000, 7000, 10,000, etc. As described above, in certain embodiments. the phosphorothioate nucleic acids herein contain one or more phosphodiester bonds. In other embodiments, the phosphorothioate nucleic acids include alternate backbones (e.g., mimics or analogs of phosphodiesters as known in the art, such as, boranophosphate, methylphosphonate, phosphoramidate, or O-methylphosphoroamidite linkages (see Eckstein, Oligonucleotides and Analogues: A Practical Approach, Oxford University Press). The phosphorothioate nucleic acids may also include one or more nucleic acid analog monomers known in the art, such as, peptide nucleic acid monomer or polymer, locked nucleic acid monomer or polymer, morpholino monomer or polymer, glycol nucleic acid monomer or polymer, or threose nucleic acid monomer or polymer. Other analog nucleic acids include those with positive backbones; non-ionic backbones, and nonribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. Phosphorothioate nucleic acids and phosphorothioate polymer backbones can be linear or branched. For example, the branched nucleic acids are repetitively branched to form higher ordered structures such as dendrimers and the like.

As used herein, a "phosphorothioate polymer backbone" is a chemical polymer with at least two phosphorothioate linkages (e.g. monothiophosphate) (e.g. linking together sugar subunits, cyclic subunits or alkyl subunits). The phosphorothioate polymer backbone may be a phosphorothioate sugar polymer, which is a phosphorothioate nucleic acid in which one or more (or all) of the chain of pentose sugars lack the bases (nucleobases) normally present in a nucleic acid. The phosphorothioate polymer backbone can include two or more phosphorothioate linkages. The phosphorothioate polymer backbone can include 5, 6, 7, 8, 9, 10, 12, 15, 25, 30, 40, 50 or more linkages and can contain up to about 100 phosphorothioate linkages. Phosphorothioate polymer backbones may also contain a larger number of linkages, e.g., 200, 300, 500, 1000, 2000, 3000, 5000, 7000, 10,000, and the like.

The phosphorothioate nucleic acids and phophorothioate polymer backbones may be partially or completely phosphorothioated. For example, 50% or more of the internucleotide linkages of a phosphorothioate nucleic acid can be phosphorothioate linkages. Optionally, 5%, 10%, 15%, 20%, 25%, 30%, 35%, 40%, 45%, 50%, 55%, 60%, 65%, 70%, 75%, 80%, 85%, 90%, 95%, or 99% of the internucleotide linkages of a phosphorothioate nucleic acid are phosphorothioate linkages. Optionally, 50%, 55%, 60%, 65%, 70%, 75%, 80%, 85%, 90%, 95%, or 99% of the internucleotide linkages of a phosphorothioate nucleic acid are phosphorothioate linkages. Optionally, 75%, 80%, 85%, 90%, 95%, or 99% of the internucleotide linkages of a phosphorothioate nucleic acid are phosphorothioate linkages. Optionally, 90%, 95%, or 99% of the internucleotide linkages of a phosphorothioate nucleic acid are phosphorothioate linkages. In embodiments, the remaining internucleotide linkages are phosphodiester linkages. In embodiments, the remaining internucleotide linkages are methylphosphonate linkages. Optionally, 100% of the internucleotide linkages of the phosphorothioate nucleic acids are phosphorothioate linkages. Similarly, 5%, 10%, 15%, 20%, 25%, 30%, 35%, 40%, 45%, 50%, 55%, 60%, 65%, 70%, 75%, 80%, 85%, 90%, 95%, or 99%, of the intersugar linkages in a phosphorothioate polymer backbone can be phosphorothioate linkages. Optionally, 50%, 55%, 60%, 65%, 70%, 75%, 80%, 85%, 90%, 95%, or 99%, of the intersugar linkages in a phosphorothioate polymer backbone can be phosphorothioate linkages. Optionally, 75%, 80%, 85%, 90%, 95%, or 99%, of the intersugar linkages in a phosphorothioate polymer backbone can be phosphorothioate linkages. Optionally, 90%, 95%, or 99%, of the intersugar linkages in a phosphorothioate polymer backbone can be phosphorothioate linkages. In embodiments, the remaining internucleotide linkages are phosphodiester linkages. In embodiments, the remaining internucleotide linkages are methylphosphonate linkages. Optionally, 100% of the intersugar linkages of the phosphorothioate polymer backbone are phosphorothioate linkages.

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art. In embodiments, the phosphorothioate nucleic acid or phosphorothioate polymer backbone is connected to a detectable label through a chemical linker.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

The phosphorothioate nucleic acids and phosphorothioate polymer backbones provided herein can include one or more reactive moieties, e.g., a covalent reactive moiety. A reactive moiety may be attached to the remainder of the phosphorothioate nucleic acids and phosphorothioate polymer backbones using any appropriate linker, such as a polymer linker known in the art or alternatively a polyethylene glygcol linker or equivalent. The linker may, in embodiments, include (i.e. be attached to) a detectable label as described herein. As used herein, the term "covalent reactive moiety" refers to a chemical moiety capable of chemically reactive with an amino acid of a non-cell penetrating protein, as described herein, to form a covalent bond and, thus, a conjugate as provided herein.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell.

The term "exogenous" refers to a molecule or substance (e.g., a compound, nucleic acid peptide, or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance (e.g., protein or peptide) that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "numbered with reference to" or "corresponding to," when used in the context of the numbering of a given amino acid or polynucleotide sequence, refer to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., Hdm2) in other proteins with different numbering systems. For example, by performing a simple sequence alignment with a protein (e.g., Hdm2) the identity and location of residues corresponding to specific positions of said protein are identified in other protein sequences aligning to said protein. For example, a selected residue in a selected protein corresponds to serine at position 116 when the selected residue occupies the same essential spatial or other structural relationship as a serine at position 116. In some embodiments, where a selected protein is aligned for maximum homology with a protein, the position in the aligned selected protein aligning with serine 116 is said to correspond to serine 116. Instead of a primary sequence alignment, a three dimensional structural alignment can also be used, e.g., where the structure of the selected protein is aligned for maximum correspondence with the serine at position 116, and the overall structures compared. In this case, an amino acid that occupies the same essential position as serine 116 in the structural model is said to correspond to the serine 116 residue.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical. This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the terms "cell-penetrating" or "cell-penetration" refer to the ability of a molecule (e.g. a protein) to pass from the extracellular environment into a cell in a significant or effective amount. Thus, a cell-penetrating conjugate is a molecule that passes from the extracellular environment, through the membrane, and into a cell.

As used herein, the terms "non-cell penetrating" or "non-cell penetration" refers to the inability of a molecule to pass from the extracellular environment into a cell in a significant or effective amount. Thus, non-cell penetrating peptides or proteins generally are not capable of passing from the extracellular environment, through the cell membrane, and into a cell in order to achieve a significant biological effect on a population of cells, organ or organism. The term does not exclude the possibility that one or more of the small number of peptides or proteins may enter the cell. However, the term refers to molecules that are generally not able to enter a cell from the extracellular environment to a significant degree. Examples of non-cell penetrating molecules and substances include, but are not limited to, large molecules such as, for example, high molecular weight proteins. Peptides or proteins can be determined to be non-cell penetrating using methods known to those of skill in the art. By way of example, a peptide or protein can be fluorescently labeled and the ability of the peptide or protein to pass from the extracellular environment into the cell can be determined in vitro by flow cytometric analysis or confocal microscopy. In some embodiments, a "non-cell penetrating protein" refers to a protein that penetrates a cell at least about 2, 3, 4, 5, 6, 7, 8, 9, 10, 20, 30, 40, 50, 60, 70, 80, 90, 100, 200, 300, 400, 500, 600, 700, 800, 900, 1000, 10,000 or 100,000 fold less than the same protein attached to a phosphorothioate nucleic acid or phosphorothioate polymer backbone. In some embodiments, a "non-cell penetrating protein" refers to a protein that does not measurably penetrate a cell.

As used herein, the term "intracellular" means inside a cell. As used herein, an "intracellular target" is a target, e.g., nucleic acid, polypeptide or other molecule (e.g., carbohydrate) that is located inside of a cell and is a target to which the non-cell penetrating proteins provided herein bind. Binding can be direct or indirect. Optionally, the non-cell penetrating protein selectively binds the intracellular target. By selectively binds, selectively binding, or specifically binding refers to the agent (e.g., a non-cell penetrating protein) binding one agent (e.g., intracellular target) to the partial or complete exclusion of other agents. By binding is meant a detectable binding at least about 1.5 times the background of the assay method. For selective or specific binding such a detectable binding can be detected for a given agent but not a control agent. Alternatively, or additionally, the detection of binding can be determined by assaying the presence of down-stream molecules or events.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIO- CONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the phosphorothioate nucleic acid and phosphorothioate backbone polymer are non-covalently attached to the protein through a non-covalent chemical reaction between a component of the phosphorothioate nucleic acid and phosphorothioate backbone polymer (e.g. a monothiophosphate) and a component of the protein (e.g. an amino acid).

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The term "activating," as used herein, refers to an nucleic acid-peptide conjugate capable of detectably increasing the expression or activity of a given gene or protein (e.g., p53). The activating nucleic acid-peptide conjugate can increase expression or activity 10%, 20%, 30%, 40%, 50%, 60%, 70%, 80%, 90% or more in comparison to a control in the absence of the activating nucleic acid. In certain instances, expression or activity is 1.5-fold, 2-fold, 3-fold, 4-fold, 5-fold, 10-fold or higher than the expression or activity in the absence of the activating nucleic acid-peptide conjugate.

As defined herein, the term "inhibition", "inhibit", "inhibiting" and the like in reference to an nucleic acid-peptide conjugate interaction means negatively affecting (e.g. decreasing) the activity or function of a protein (e.g., Hdm2) relative to the activity or function of the protein in the absence of the inhibitor. In embodiments inhibition refers to reduction of a disease or symptoms of disease. Thus, in embodiments, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition or inhibiting refers to reduction of protein degradation. Thus, in embodiments, inhibition includes decreasing or preventing the degradation of a protein (e.g., p53). In embodiments, inhibition or inhibiting refers to decreasing or preventing posttranslational modifications of a protein. Therefore, in embodiments, inhibition includes or decreasing preventing, for example, phosphorylation or acetylation of a protein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a non-cell penetrating peptide as described herein and an intracellular target (e.g., Hdm2).

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "control" or "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage-like synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

The terms "subject," "patient," "individual," etc. are not intended to be limiting and can be generally interchanged. That is, an individual described as a "patient" does not necessarily have a given disease, but may be merely seeking medical advice.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

Nucleic Acid-Peptide Conjugates

Provided herein are, inter alia, nucleic acid-peptide conjugates including a non-cell penetrating protein attached at its C-terminus to a phosphorothioate nucleic acid. Attachment of the phosphorothioate nucleic acid to the non-cell penetrating protein conveys stability to and allows for efficient intracellular delivery of the non-cell penetrating peptide. Upon entry into a cell, the non-cell penetrating peptides provided herein may target and modify the activity of intracellular molecules involved in disease pathology (e.g., Mdm2, Hdm2 or p53) thereby improving disease outcome. The Hdm2 targeting peptides provided herein are, inter alia, capable of reducing the phosphorylation of Hdm2 and thereby decreasing ubiquitination of p53. The nucleic acid-peptide conjugates provided herein including embodiments thereof are useful, inter alia, for the treatment of cancer.

In an aspect is provided a nucleic acid-peptide conjugate including: (i) a non-cell penetrating peptide; (ii) a phosphorothioate nucleic acid; and (iii) a chemical linker attaching the phosphorothioate nucleic acid to the C-terminus of the non-cell penetrating peptide; wherein the phosphorothioate nucleic acid enhances intracellular delivery of the non-cell penetrating peptide.

As used herein, the term "C-terminus" is synonymous with carboxyl-terminus, carboxy-terminus, C-terminal tail, C-terminal end, and COOH-terminus, is used in accordance with its ordinary meaning in biology and refers to the termination moiety of an amino acid sequence. For example, the C-terminus may refer to the last amino acid in an amino acid sequence, e.g.,

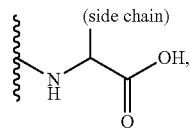

wherein side chain refers to the amino acid side chain). In embodiments, the C-terminus includes a carboxylic acid moiety.

In embodiments, the non-cell penetrating peptide is about 5, 10, 15, 20 or 25 amino acids in length. In embodiments, the non-cell penetrating peptide is about 5 amino acids in length. In embodiments, the non-cell penetrating peptide is 5 amino acids in length. In embodiments, the non-cell penetrating peptide is about 8 amino acids in length. In embodiments, the non-cell penetrating peptide is 8 amino acids in length. In embodiments, the non-cell penetrating peptide is about 10 amino acids in length. In embodiments, the non-cell penetrating peptide is 10 amino acids in length. In embodiments, the non-cell penetrating peptide is about 11 amino acids in length. In embodiments, the non-cell penetrating peptide is 11 amino acids in length. In embodiments, the non-cell penetrating peptide is about 15 amino acids in length. In embodiments, the non-cell penetrating peptide is 15 amino acids in length. In embodiments, the non-cell penetrating peptide is about 22 amino acids in length. In embodiments, the non-cell penetrating peptide is 22 amino acids in length. In embodiments, the non-cell penetrating peptide is about 20 amino acids in length. In embodiments, the non-cell penetrating peptide is 20 amino acids in length. In embodiments, the non-cell penetrating peptide is about 25 amino acids in length. In embodiments, the non-cell penetrating peptide is 25 amino acids in length.

In embodiments, the non-cell penetrating peptide is at least 5 (e.g., 5, 6, 7, 8, 9, 10, 11, 12, 13, 14, 15, 16, 17, 18, 19, 20, 21, 22, 23, 24, 25, 26, 26, 28, 29, 30, 35, 40, 45, 50) amino acids in length. In embodiments, the non-cell penetrating peptide is at least 6 amino acids in length. In embodiments, the non-cell penetrating peptide is at least 7 amino acids in length. In embodiments, the non-cell penetrating peptide is at least 8 amino acids in length. In embodiments, the non-cell penetrating peptide is at least 9 amino acids in length. In embodiments, the non-cell penetrating peptide is at least 10 amino acids in length. In embodiments, the non-cell penetrating peptide is at least at least 11 amino acids in length. In embodiments, the non-cell penetrating peptide is at least 12 amino acids in length. In embodiments, the non-cell penetrating peptide is at least 13 amino acids in length. In embodiments, the non-cell penetrating peptide is at least 14 amino acids in length. In embodiments, the non-cell penetrating peptide is at least 15 amino acids in length. In embodiments, the non-cell penetrating peptide is at least 16 amino acids in length. In embodiments, the non-cell penetrating peptide is at least 17 amino acids in length. In embodiments, the non-cell penetrating peptide is at least 18 amino acids in length. In embodiments, the non-cell penetrating peptide is at least 19 amino acids in length. In embodiments, the non-cell penetrating peptide is at least 20 amino acids in length. In embodiments, the non-cell penetrating peptide is at least 21 amino acids in length. In embodiments, the non-cell penetrating peptide is at least 22 amino acids in length. In embodiments, the non-cell penetrating peptide is at least 23 amino acids in length. In embodiments, the non-cell penetrating peptide is at least 24 amino acids in length. In embodiments, the non-cell penetrating peptide is at least 25 amino acids in length. In embodiments, the non-cell penetrating peptide is at least 26 amino acids in length. In embodiments, the non-cell penetrating peptide is at least 27 amino acids in length. In embodiments, the non-cell penetrating peptide is at least 28 amino acids in length. In embodiments, the non-cell penetrating peptide is at least 29 amino acids in length. In embodiments, the non-cell penetrating peptide is at least 30 amino acids in length. In embodiments, the non-cell penetrating peptide is at least 35 amino acids in length. In embodiments, the non-cell penetrating peptide is at least 40 amino acids in length. In embodiments, the non-cell penetrating peptide is at least 45 amino acids in length. In embodiments, the non-cell penetrating peptide is at least 50 amino acids in length.

In embodiments, the non-cell penetrating peptide is about 14 amino acids in length. In embodiments, the non-cell penetrating peptide is 14 amino acids in length.

In embodiments, the non-cell penetrating peptide has a molecular weight of less than about 25 kD (e.g., 24, 23, 22, 21, 20, 19, 18, 17, 16, 15, 14, 13, 12, 11, 10, 5, 1 kD). In embodiments, the non-cell penetrating peptide has a molecular weight of less than about 24 kD. In embodiments, the non-cell penetrating peptide has a molecular weight of less than about 23 kD. In embodiments, the non-cell penetrating peptide has a molecular weight of less than about 22 kD. In embodiments, the non-cell penetrating peptide has a molecular weight of less than about 21 kD. In embodiments, the non-cell penetrating peptide has a molecular weight of less than about 20 kD. In embodiments, the non-cell penetrating peptide has a molecular weight of less than about 19 kD. In embodiments, the non-cell penetrating peptide has a molecular weight of less than about 18 kD. In embodiments, the non-cell penetrating peptide has a molecular weight of less than about 17 kD. In embodiments, the non-cell penetrating peptide has a molecular weight of less than about 16 kD. In embodiments, the non-cell penetrating peptide has a molecular weight of less than about 15 kD. In embodiments, the non-cell penetrating peptide has a molecular weight of less than about 14 kD. In embodiments, the non-cell penetrating peptide has a molecular weight of less than about 13 kD. In embodiments, the non-cell penetrating peptide has a molecular weight of less than about 12 kD. In embodiments, the non-cell penetrating peptide has a molecular weight of less than about 11 kD. In embodiments, the non-cell penetrating peptide has a molecular weight of less than about 10 kD. In embodiments, the non-cell penetrating peptide has a molecular weight of less than about 5 kD. In embodiments, the non-cell penetrating peptide has a molecular weight of less than about 1 kD. In embodiments, the non-cell penetrating peptide has a molecular weight of less than 25 kD. In embodiments, the non-cell penetrating peptide has a molecular weight of less than 24 kD. In embodiments, the non-cell penetrating peptide has a molecular weight of less than 23 kD. In embodiments, the non-cell penetrating peptide has a molecular weight of less than 22 kD. In embodiments, the non-cell penetrating peptide has a molecular weight of less than 21 kD. In embodiments, the non-cell penetrating peptide has a molecular weight of less than 20 kD. In embodiments, the non-cell penetrating peptide has a molecular weight of less than 19 kD. In embodiments, the non-cell penetrating peptide has a molecular weight of less than 18 kD. In embodiments, the non-cell penetrating peptide has a molecular weight of less than 17 kD. In embodiments, the non-cell penetrating peptide has a molecular weight of less than 16 kD. In embodiments, the non-cell penetrating peptide has a molecular weight of less than 15 kD. In embodiments, the non-cell penetrating peptide has a molecular weight of less than 14 kD. In embodiments, the non-cell penetrating peptide has a molecular weight of less than 13 kD. In embodiments, the non-cell penetrating peptide has a molecular weight of less than 12 kD. In embodiments, the non-cell penetrating peptide has a molecular weight of less than 11 kD. In embodiments, the non-cell penetrating peptide has a molecular weight of less than 10 kD. In embodiments, the non-cell penetrating peptide has a molecular weight of less than about 5 kD. In embodiments, the non-cell penetrating peptide has a molecular weight of less than 1 kD.

In embodiments, the non-cell penetrating peptide is not an antibody or an antibody fragment. In embodiments, the non-cell penetrating peptide is less than about 25 amino acids in length. In embodiments, the non-cell penetrating peptide is less than 25 amino acids in length. In embodiments, the non-cell penetrating peptide is less than about 24 amino acids in length. In embodiments, the non-cell penetrating peptide is less than 24 amino acids in length. In embodiments, the non-cell penetrating peptide is less than about 23 amino acids in length. In embodiments, the non-cell penetrating peptide is less than 23 amino acids in length. In embodiments, the non-cell penetrating peptide is less than about 22 amino acids in length. In embodiments, the non-cell penetrating peptide is less than 22 amino acids in length. In embodiments, the non-cell penetrating peptide is less than about 21 amino acids in length. In embodiments, the non-cell penetrating peptide is less than 21 amino acids in length. In embodiments, the non-cell penetrating peptide is less than about 20 amino acids in length. In embodiments, the non-cell penetrating peptide is less than 20 amino acids in length. In embodiments, the non-cell penetrating peptide is less than about 15 amino acids in length. In embodiments, the non-cell penetrating peptide is less than 15 amino acids in length. In embodiments, the non-cell penetrating peptide is less than about 10 amino acids in length. In embodiments, the non-cell penetrating peptide is less than 10 amino acids in length.

The non-cell penetrating peptides provided herein including embodiments thereof may include modified amino acids. Examples of modified amino acids include without limitation, chemically modified naturally occurring amino acids, chemically modified synthetic amino acids, as well as chemically modified amino acid analogs and amino acid mimetics. Modified naturally occurring amino acids may be modified post-translationally in a cell or synthetically in a reaction vessel. The presence of a modified amino acid may convey alternate functional and/or structural features to the peptide it forms part of relative to the corresponding non-modified amino acid.

In embodiments, the modified amino acid is an alanine. In embodiments, the modified amino acid is aminoisobutyric acid.

The non-cell penetrating peptides provided herein including embodiments thereof may be linear or cyclic peptides. Thus, in embodiments, the non-cell penetrating peptide is a cyclized peptide. In embodiments, the non-cell penetrating peptide is a linear peptide.

In embodiments, the non-cell penetrating peptide includes the sequence of SEQ ID NO:3. In embodiments, the non-cell penetrating peptide is the sequence of SEQ ID NO:3.

The non-cell penetrating peptides provided herein including embodiments thereof are useful for the treatment of cancer by modifying the activity of intracellular molecules. Thus, in embodiments, the non-cell penetrating peptide binds an intracellular target. In embodiments, the intracellular target is an oncogene. In embodiments, the intracellular target is an E3 ubiquitin ligase. In embodiments, the intracellular target is Hdm2. In embodiments, the intracellular target is an Hdm2 protein including the amino acid sequence of SEQ ID NO:2. In embodiments, the intracellular target is an Hdm2 protein consisting of the amino acid sequence of SEQ ID NO:2.

The term "Hdm2", also known as E3 ubiquitin ligase Mdm2 or Mdm2, as used herein refers to any recombinant or naturally-occurring forms of the Hdm2 protein or variants or homologs thereof that maintain Hdm2 activity (e.g. within at least 50%, 80%, 90%, 95%, 96%, 97%, 98%, 99% or 100% activity compared to Hdm2). In some aspects, the variants or homologs have at least 90%, 95%, 96%, 97%, 98%, 99% or 100% amino acid sequence identity across the whole sequence or a portion of the sequence (e.g. a 10, 20, 50, 100, 150 or 200 continuous amino acid portion) compared to a naturally occurring Hdm2 polypeptide. In embodiments, Hdm2 is substantially identical to the protein identified by the UniProt reference number Q00987 or a variant or homolog having substantial identity thereto. In embodiments, Hdm2 protein includes the sequence of SEQ ID NO:2. In embodiments, Hdm2 is the sequence of SEQ ID NO:2.

In embodiments, the non-cell penetrating peptide competes with a cellular protein or cellular peptide for binding an intracellular target. A "cellular protein or cellular peptide" refers to a protein or peptide that is endogenous to a cell (i.e., is native to, or originates within, a given cell). In embodiments, the cellular protein or cellular peptide includes the sequence of SEQ ID NO:1. In embodiments, the cellular protein or cellular peptide is the sequence of SEQ ID NO:1. In embodiments, the cellular protein or cellular peptide is a p53 protein or fragment thereof. A "p53 protein" or "p53" as referred to herein includes any of the recombinant or naturally-occurring forms of cellular tumor antigen p53 (p53) or variants or homologs thereof that maintain p53 activity (e.g. within at least 50%, 80%, 90%, 95%, 96%, 97%, 98%, 99% or 100% activity compared to p53). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring p53. In embodiments, p53 is substantially identical to the protein identified by the UniProt reference number P04637 or a variant or homolog having substantial identity thereto. In embodiments, p53 includes the sequence of SEQ ID NO:1. In embodiments, p53 is the sequence of SEQ ID NO:1.

In embodiments, the phosphorothioate nucleic acid is about 10, 20, 30, 40, 50, 60, 70, 80, 90, 100 or more nucleic acid residues in length. In embodiments, the phosphorothioate nucleic acid is about 10 nucleic acid residues in length. In embodiments, the phosphorothioate nucleic acid is about 20 nucleic acid residues in length. In embodiments, the phosphorothioate nucleic acid is about 30 nucleic acid residues in length. In embodiments, the phosphorothioate nucleic acid is about 40 nucleic acid residues in length. In embodiments, the phosphorothioate nucleic acid is about 50 nucleic acid residues in length. In embodiments, the phosphorothioate nucleic acid is about 60 nucleic acid residues in length. In embodiments, the phosphorothioate nucleic acid is about 70 nucleic acid residues in length. In embodiments, the phosphorothioate nucleic acid is about 80 nucleic acid residues in length. In embodiments, the phosphorothioate nucleic acid is about 90 nucleic acid residues in length. In embodiments, the phosphorothioate nucleic acid is about 100 nucleic acid residues in length. In embodiments, the phosphorothioate nucleic acid is about more than 100 nucleic acid residues in length. In embodiments, the phosphorothioate nucleic acid is 10, 20, 30, 40, 50, 60, 70, 80, 90, 100 or more nucleic acid residues in length.

In embodiments, the phosphorothioate nucleic acid is from about 10 to about 30 nucleic acid residues in length. In embodiments, the phosphorothioate nucleic acid is from about 11 to about 30 nucleic acid residues in length. In embodiments, the phosphorothioate nucleic acid is from about 12 to about 30 nucleic acid residues in length. In embodiments, the phosphorothioate nucleic acid is from about 13 to about 30 nucleic acid residues in length. In embodiments, the phosphorothioate nucleic acid is from about 14 to about 30 nucleic acid residues in length. In embodiments, the phosphorothioate nucleic acid is from about 15 to about 30 nucleic acid residues in length. In embodiments, the phosphorothioate nucleic acid is from about 16 to about 30 nucleic acid residues in length. In embodiments, the phosphorothioate nucleic acid is from about 17 to about 30 nucleic acid residues in length. In embodiments, the phosphorothioate nucleic acid is from about 18 to about 30 nucleic acid residues in length. In embodiments, the phosphorothioate nucleic acid is from about 19 to about 30 nucleic acid residues in length. In embodiments, the phosphorothioate nucleic acid is from about 20 to about 30 nucleic acid residues in length. In embodiments, the phosphorothioate nucleic acid is from about 21 to about 30 nucleic acid residues in length. In embodiments, the phosphorothioate nucleic acid is from about 22 to about 30 nucleic acid residues in length. In embodiments, the phosphorothioate nucleic acid is from about 23 to about 30 nucleic acid residues in length. In embodiments, the phosphorothioate nucleic acid is from about 24 to about 30 nucleic acid residues in length. In embodiments, the phosphorothioate nucleic acid is from about 25 to about 30 nucleic acid residues in length. In embodiments, the phosphorothioate nucleic acid is from about 26 to about 30 nucleic acid residues in length. In embodiments, the phosphorothioate nucleic acid is from about 27 to about 30 nucleic acid residues in length. In embodiments, the phosphorothioate nucleic acid is from about 28 to about 30 nucleic acid residues in length. In embodiments, the phosphorothioate nucleic acid is from about 29 to about 30 nucleic acid residues in length. In embodiments, the phosphorothioate nucleic acid is about 30 nucleic acid residues in length.

In embodiments, the phosphorothioate nucleic acid is from about 10 to about 29 nucleic acid residues in length. In embodiments, the phosphorothioate nucleic acid is from about 10 to about 28 nucleic acid residues in length. In embodiments, the phosphorothioate nucleic acid is from about 10 to about 27 nucleic acid residues in length. In embodiments, the phosphorothioate nucleic acid is from about 10 to about 26 nucleic acid residues in length. In embodiments, the phosphorothioate nucleic acid is from about 10 to about 25 nucleic acid residues in length. In embodiments, the phosphorothioate nucleic acid is from about 10 to about 24 nucleic acid residues in length. In embodiments, the phosphorothioate nucleic acid is from about 10 to about 23 nucleic acid residues in length. In embodiments, the phosphorothioate nucleic acid is from about 10 to about 22 nucleic acid residues in length. In embodiments, the phosphorothioate nucleic acid is from about 10 to about 21 nucleic acid residues in length. In embodiments, the phosphorothioate nucleic acid is from about 10 to about 20 nucleic acid residues in length. In embodiments, the phosphorothioate nucleic acid is from about 10 to about 19 nucleic acid residues in length. In embodiments, the phosphorothioate nucleic acid is from about 10 to about 18 nucleic acid residues in length. In embodiments, the phosphorothioate nucleic acid is from about 10 to about 17 nucleic acid residues in length. In embodiments, the phosphorothioate nucleic acid is from about 10 to about 16 nucleic acid residues in length. In embodiments, the phosphorothioate nucleic acid is from about 10 to about 15 nucleic acid residues in length. In embodiments, the phosphorothioate nucleic acid is from about 10 to about 14 nucleic acid residues in length. In embodiments, the phosphorothioate nucleic acid is from about 10 to about 13 nucleic acid residues in length. In embodiments, the phosphorothioate nucleic acid is from about 10 to about 12 nucleic acid residues in length. In embodiments, the phosphorothioate nucleic acid is from about 10 to about 11 nucleic acid residues in length. In embodiments, the phosphorothioate nucleic acid is about 10 nucleic acid residues in length. In embodiments, the phosphorothioate nucleic acid is 10, 11, 12, 13, 14, 15, 16, 17, 18, 19, 20, 21, 22, 23, 24, 25, 26, 27, 28, 29, or 30 nucleic acid residues in length.

In embodiments, the phosphorothioate nucleic acid is about 20 nucleic acid residues in length. In embodiments, the phosphorothioate nucleic acid is 20 nucleic acid residues in length.

In embodiments, the phosphorothioate nucleic acid is a single stranded nucleic acid. In embodiments, the phosphorothioate nucleic acid is a phosphorothioate deoxyribonucleic acid.

In embodiments, the chemical linker is a covalent linker. In embodiments, the linker includes the structure of formula:

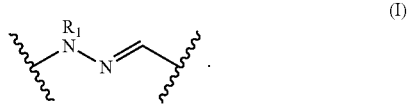

In formula (I), $R^1$ is hydrogen, halogen, —$CF_3$, —CN, —$CCl_3$, —COOH, —$CH_2$COOH, —$CONH_2$, —OH, —SH, —$NO_2$, —$NH_2$, —NH$NH_2$, —O$NH_2$, —NHC=(O) NH$NH_2$, substituted (e.g., substituted with substituent group(s), size-limited substituent group(s), or lower substituent group(s)) or unsubstituted alkyl, substituted (e.g., substituted with substituent group(s), size-limited substituent group(s), or lower substituent group(s)) or unsubstituted heteroalkyl, substituted (e.g., substituted with substituent group(s), size-limited substituent group(s), or lower substituent group(s)) or unsubstituted cycloalkyl, substituted (e.g., substituted with substituent group(s), size-limited substituent group(s), or lower substituent group(s)) or unsubstituted heterocycloalkyl, substituted (e.g., substituted with substituent group(s), size-limited substituent group(s), or lower substituent group(s)) or unsubstituted aryl, or substituted (e.g., substituted with substituent group(s), size-limited substituent group(s), or lower substituent group(s)) or unsubstituted heteroaryl.

In embodiments, le is hydrogen, halogen, —$CF_3$, —CN, —$CCl_3$, —COOH, —$CH_2$COOH, —$CONH_2$, —OH, —SH, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, the linker is -$L^1$-$L^2$-$L^3$-$L^4$-$L^5$-$L^6$-$L^7$-. In embodiments, $L^1$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^2$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^3$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^4$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^5$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^6$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^7$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, the linker is a non-immunogenic linker. In embodiments, the linker is substituted with a detectable moiety.

In embodiments, the conjugate includes a detectable moiety. In embodiments, the detectable moiety is attached to the non-cell penetrating peptide. In embodiments, the detectable moiety is attached to the phosphorothioate nucleic acid. In embodiments, the detectable moiety forms part of the linker. In embodiments, the detectable moiety is covalently attached to the linker.

In embodiments, the conjugate as provided herein including embodiments thereof is bound to an intracellular target.

In an aspect is provided a cell including a peptide conjugate as described herein including embodiments thereof.

In one embodiment, the non-cell penetrating peptide is a peptide of SEQ ID NO:3, the phosphorthioate nucleic acid is a single stranded nucleic acid 20 nucleic acid residues in length and the chemical linker includes the structure of formula (I).

Pharmaceutical Compositions

The conjugates provided herein including embodiments thereof are further contemplated as forming part of a pharmaceutical composition. Therefore, in an aspect is provided a pharmaceutical composition including the peptide conjugate as described herein including embodiments thereof and a pharmaceutically acceptable carrier.

Pharmaceutical compositions provided by the present invention include compositions wherein the active ingredient (e.g. compositions described herein, including embodiments thereof) is contained in a therapeutically effective amount, i.e., in an amount effective to achieve its intended purpose. The actual amount effective for a particular application will depend, inter alia, on the condition being treated. When administered in methods to treat a disease, the conjugates described herein will contain an amount of active ingredient effective to achieve the desired result, e.g., modulating the activity of a target molecule, and/or reducing, eliminating, or slowing the progression of disease symptoms. Determination of a therapeutically effective amount of a conjugate of the invention is within the capabilities of those skilled in the art.

The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., the conjugates provided herein including embodiments thereof) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Methods of Treatment Cancer

The conjugates as provided herein including embodiments thereof are useful, inter alia, for the treatment of cancer. Thus, in an aspect, a method for treating cancer in a subject in need thereof is provided. The method includes administering to the subject a therapeutically effective amount of a cell penetrating peptide conjugate as described herein including embodiments thereof, thereby treating the cancer in the subject.

In embodiments, the cancer is breast cancer, prostate cancer, ovarian cancer, brain cancer, pancreatic cancer, melanoma, colon cancer, gastric cancer, head-and-neck cancer, liver cancer, lung cancer, cervical cancer, sarcoma, leukemia, lymphoma, multiple myeloma.

Methods of Inhibiting Degradation of P53 in a Cancer Cell p53 is an important tumor suppressor protein that can prevent transformation of healthy cells to cancerous cells. A loss or decrease in p53 protein can compromise the health of a cell and lead to uncontrolled cell growth (i.e., cancer). Therefore, in an aspect is provided a method of inhibiting degradation of p53 in a cancer cell, the method including contacting a cancer cell with an effective amount of a cell penetrating peptide conjugate as described herein including embodiments thereof, thereby inhibiting degradation of p53 in the cancer cell.

Methods of Inhibiting Hdm2 Phosphorylation in a Cell

Phosphorylation of Hdm2 (Mdm2) at serine 116 (S116) is a critical posttranslational modification involved in mediating the interaction of Hdm2 and p53. Hdm2 interaction with p53 can result in p53 ubiquitination and degradation which can lead to decreased tumor suppression. The conjugates provided herein including embodiments thereof are useful, inter alia, in reducing the interaction of Hdm2 and p53 by inhibiting phosphorylation of Hdm2. Therefore, in an aspect is provided a method of inhibiting Hdm2 phosphorylation in a cell, the method including contacting a cell with an effective amount of a cell penetrating peptide conjugate as described herein including embodiments thereof, thereby inhibiting Hdm2 phosphorylation in the cell.

Methods of Delivering a Non-Cell Penetrating Peptide into a Cell

The conjugates provided herein including embodiments thereof are, inter alia, useful for delivering non-cell penetrating peptides into a cell. In an aspect is provided a method of delivering a non-cell penetrating peptide into a cell, the method including contacting a cell with a cell penetrating peptide conjugate as provided herein including embodiments thereof, thereby delivering the non-cell penetrating peptide into the cell.

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Figures 1, 2A:
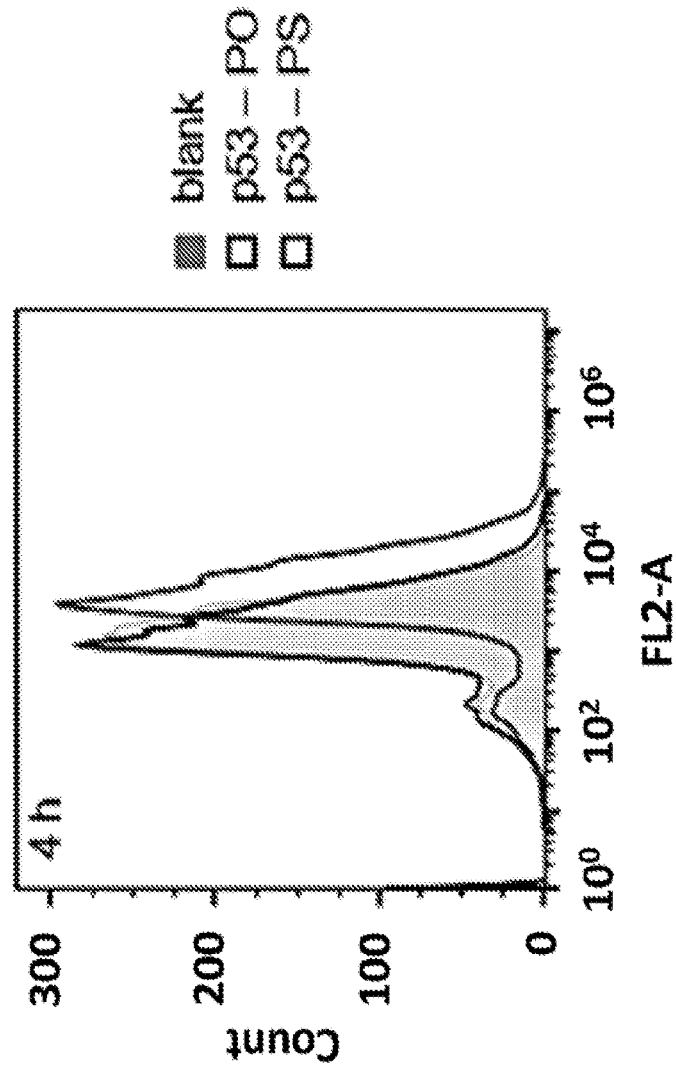
FIG. 1: Mdm2 targeting peptide sequence (also referred to herein as p53 peptide sequence; SEQ ID NO:3). Shown is the three letter amino acid sequence targeting the p53/Mdm2 interaction circuit. The peptide was extended at its C-terminus by a linker followed by a 20meric ssDNA stretch. The non-specific sequences of PS-ssDNA 20mer (SEQ ID NO:4) is also shown. It is critical that the sugar-phosphate backbone is phosphorothioated (PS; upper) indicated by (*) to achieve cellular internalization. The phosphodiester ssDNA sequence is used as a non-internalizing control sequence attached to the Mdm2 targeting peptide (p53 peptide) (PO; lower).
FIGS. 2A-2B: PS-modified p53/Mdm2 targeting peptide (SEQ ID NO:3) readily penetrates cancer cells.
Figure 2B:
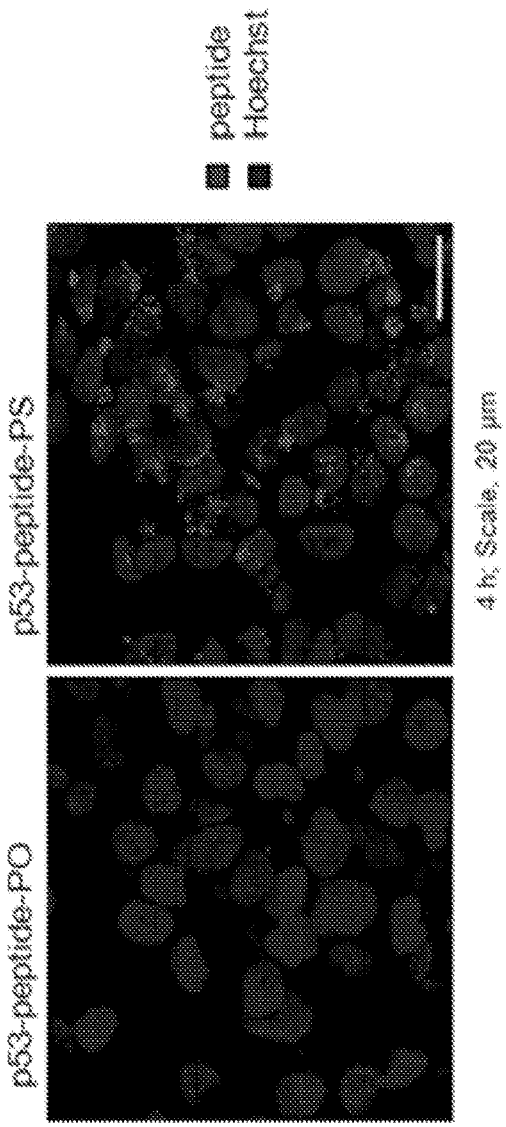
Figure 3B:
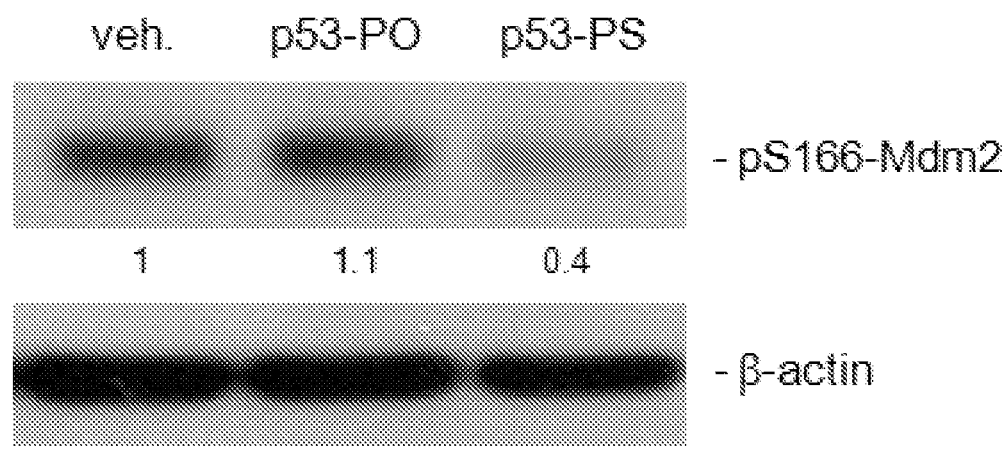
Figure 3C:
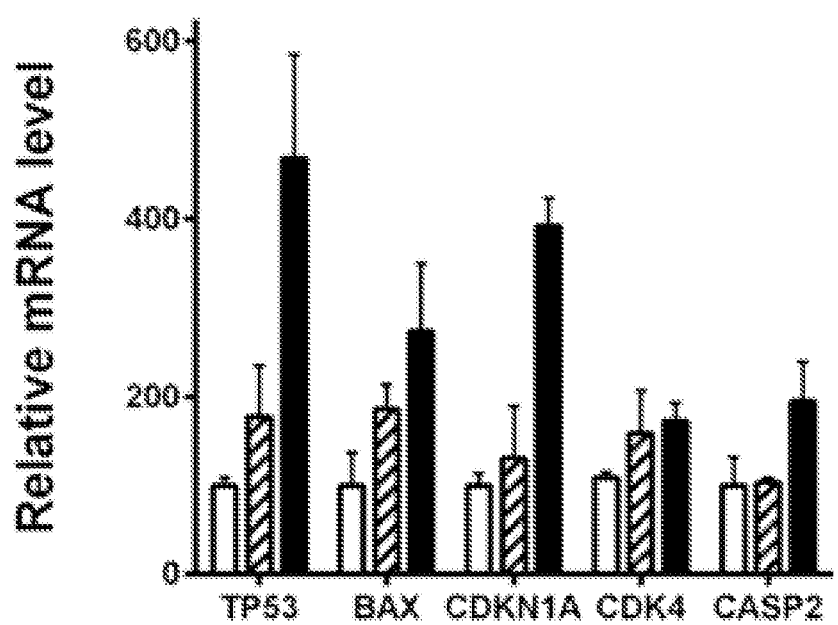

Example 1: A P53/Mdm2 Targeting Cell-Penetrating Peptide for the Benefit of Cancer Therapy The tumor suppressor protein p53 is known to exert potent antitumor activity. However, in a broad variety of tumor tissue and tumor associated tissue, the protein expression of p53 is dampened by interaction with Mdm2/Hdm2 resulting in p53 ubiquitination and subsequent degradation. Applicants disclose a peptide sequence extended by phosphorothioated ssDNA (FIG. 1) which significantly reduces tumor growth activity (FIGS. 3A-3C) once it undergoes cellular internalization (FIGS. 2A-2B), and reduces Mdm2 serine phosphorylation at S116 which is the critical post-translational modification mediating interaction of Mdm2 and p53 (FIG. 3B).

```
INFORMAL SEQUENCE LISTING
p53 polypeptide (SEQ ID NO: 1):
MEEPQSDPSVEPPLSQETFSDLWKLLPENNVLSPLPSQAMDDLMLSPDDI

EQWFTEDPGPDEAPRMPEAAPPVAPAPAAPTPAAPAPAPSWPLSSSVPSQ

KTYQGSYGFRLGFLHSGTAKSVTCTYSPALNKMFCQLAKTCPVQLWVDST

PPPGTRVRAMAIYKQSQHMTEVVRRCPHHERCSDSDGLAPPQHLIRVEGN

LRVEYLDDRNTFRHSVVVPYEPPEVGSDCTTIHYNYMCNSSCMGGMNRRP
```

```
-continued
ILTIITLEDSSGNLLGRNSFEVRVCACPGRDRRTEEENLRKKGEPHHELP

PGSTKRALPNNTSSSPQPKKKPLDGEYFTLQIRGRERFEMFRELNEALEL

KDAQAGKEPGGSRAHSSHLKSKKGQSTSRHKKLMFKTEGPDSD

Hdm2 polypeptide (SEQ ID NO: 2):
MCNTNMSVPTDGAVTTSQIPASEQETLVRPKPLLLKLLKSVGAQKDTYTM

KEVLFYLGQYIMTKRLYDEKQQHIVYCSNDLLGDLFGVPSFSVKEHRKIY

TMIYRNLVVVNQQESSDSGTSVSENRCHLEGGSDQKDLVQELQEEKPSSS

HLVSRPSTSSRRRAISETEENSDELSGERQRKRHKSDSISLSFDESLALC

VIREICCERSSSSESTGTPSNPDLDAGVSEHSGDWLDQDSVSDQFSVEFE

VESLDSEDYSLSEEGQELSDEDDEVYQVTVYQAGESDTDSFEEDPEISLA

DYWKCTSCNEMNPPLPSHCNRCWALRENWLPEDKGKDKGEISEKAKLENS

TQAEEGFDVPDCKKTIVNDSRESCVEENDDKITQASQSQESEDYSQPSTS

SSIIYSSQEDVKEFEREETQDKEESVESSLPLNAIEPCVICQGRPKNGCI

VHGKTGHLMACFTCAKKLKKRNKPCPVCRQPIQMIVLTYFP p53 modified peptide (Mdm2 targeting peptide)
(SEQ ID NO: 3):
Ac-Leu-Thr-Phe-Aib-Glu-Tyr-Trp-Aib-Gln-Leu-Aib- Ser-Ala
(Ac is an acetyl group at the N-terminus and Aib
is aminoisobutyric acid)

ssDNA 20mer (SEQ ID NO: 4):
TCCATGAGCTTCCTGATGCT
```

P EMBODIMENTS

P embodiment 1. An nucleic acid-peptide conjugate comprising:
(i) a non-cell penetrating peptide;
(ii) a phosphorothioate nucleic acid; and
(iii) a chemical linker attaching said phosphorothioate nucleic acid to said C-terminus of said non-cell penetrating peptide;
wherein said phosphorothioate nucleic acid enhances intracellular delivery of said non-cell penetrating peptide.

P embodiment 2. The conjugate of P embodiment 1, wherein said non-cell penetrating peptide is about 5, 10, 15, 20 or 25 amino acids in length.

P embodiment 3. The conjugate of one of P embodiments 1-2, wherein said non-cell penetrating peptide is at least 5 amino acids in length.

P embodiment 4. The conjugate of one of P embodiments 1-3, wherein said non-cell penetrating peptide is about 14 amino acids in length.

P embodiment 5. The conjugate of one of P embodiments 1-4, wherein said non-cell penetrating peptide has a molecular weight of less than about 25 kD.

P embodiment 6. The conjugate of one of P embodiments 1-5, wherein said non-cell penetrating peptide comprises a modified amino acid.

P embodiment 7. The conjugate of P embodiment 6, wherein said modified amino acid is an alanine.

P embodiment 8. The conjugate of P embodiment 7 or 8, wherein said modified amino acid is aminoisobutyric acid.

P embodiment 9. The conjugate of one of P embodiments 1-8, wherein said non-cell penetrating peptide is a cyclized peptide.

P embodiment 10. The conjugate of one of P embodiments 1-9, wherein said non-cell penetrating peptide comprises the sequence of SEQ ID NO:3.

P embodiment 11. The conjugate of one of P embodiments 1-10, wherein said non-cell penetrating peptide is the sequence of SEQ ID NO:3.

P embodiment 12. The conjugate of one of P embodiments 1-11, wherein said non-cell penetrating peptide binds an intracellular target.

P embodiment 13. The conjugate of P embodiment 12, wherein said intracellular target is an oncogene.

P embodiment 14. The conjugate of P embodiment 12 or 13, wherein said intracellular target is an E3 ubiquitin ligase.

P embodiment 15. The conjugate of one of P embodiments 12-14, wherein said intracellular target is Hdm2.

P embodiment 16. The conjugate of one of P embodiments 12-15, wherein said intracellular target is an Hdm2 protein comprising the amino acid sequence of SEQ ID NO:2.

P embodiment 17. The conjugate of one of P embodiments 1-16, wherein said non-cell penetrating peptide is a peptide which competes with a protein or peptide for binding an intracellular target.

P embodiment 18. The conjugate of P embodiment 17, wherein said protein or peptide comprises the sequence of SEQ ID NO:1.

P embodiment 19. The conjugate of P embodiment 17 or 18, wherein said protein or peptide is a p53 protein or fragment thereof.

P embodiment 20. The conjugate of one of P embodiments 1-19, wherein said phosphorothioate nucleic acid is about 10, 20, 30, 40, 50, 60, 70, 80, 90, 100 or more nucleic acid residues in length.

P embodiment 21. The conjugate of one of P embodiments 1-20, wherein said phosphorothioate nucleic acid is from about 10 to about 30 nucleic acid residues in length.

P embodiment 22. The conjugate of one of P embodiments 1-21, wherein said phosphorothioate nucleic acid is about 20 nucleic acid residues in length.

P embodiment 23. The conjugate of one of P embodiments 1-22, wherein said phosphorothioate nucleic acid is a single stranded nucleic acid.

P embodiment 24. The conjugate of one of P embodiments 1-23, wherein said phosphorothioate nucleic acid is a phosphorothioate deoxyribonucleic acid.

P embodiment 25. The conjugate of one of P embodiments 1-24, wherein said chemical linker is a covalent linker.

P embodiment 26. The conjugate of one of P embodiments 1-25, wherein said linker has the structure of formula:

(I)

wherein $R^1$ is hydrogen, halogen, —$CF_3$, —CN, —$CCl_3$, —COOH, —$CH_2COOH$, —$CONH_2$, —OH, —SH. —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

P embodiment 27. The conjugate of one of P embodiments 1-26, wherein said linker is a non-immunogenic linker.

P embodiment 28. The conjugate of one of P embodiments 1-26, wherein said conjugate comprises a detectable moiety.

P embodiment 29. The conjugate of P embodiment 28, wherein said detectable moiety is attached to said non-cell penetrating peptide.

P embodiment 30. The conjugate of P embodiment 28, wherein said detectable moiety is attached to said phosphorothioate nucleic acid.

P embodiment 31. The conjugate of any one of P embodiments 1-30, bound to an intracellular target.

P embodiment 32. A cell comprising a peptide conjugate of any one of P embodiments 1-30.

P embodiment 33. A pharmaceutical composition comprising a peptide conjugate of any one of P embodiments 1-30 and a pharmaceutically acceptable carrier.

P embodiment 34. A method of treating cancer in a subject in need thereof, said method comprising administering to said subject a therapeutically effective amount of a cell penetrating peptide conjugate of one of P embodiments 1-30, thereby treating said cancer in said subject.

P embodiment 35. The method of P embodiment 34, wherein said cancer is breast cancer, prostate cancer, ovarian cancer, brain cancer, pancreatic cancer, melanoma, colon cancer, gastric cancer, head-and-neck cancer, liver cancer, lung cancer, cervical cancer, sarcoma, leukemia, lymphoma, multiple myeloma.

P embodiment 36. A method of inhibiting degradation of p53 in a cancer cell, said method comprising contacting a cancer cell with an effective amount of a cell penetrating peptide conjugate of one of P embodiments 1-30, thereby inhibiting degradation of p53 in said cancer cell.

P embodiment 37. A method of inhibiting Hdm2 phosphorylation in a cell, said method comprising contacting a cell with an effective amount of a cell penetrating peptide conjugate of one of P embodiments 1-30, thereby inhibiting Hdm2 phosphorylation in said cell.

P embodiment 38. A method of delivering a non-cell penetrating peptide into a cell, said method comprising contacting a cell with a cell penetrating peptide conjugate of any one of P embodiments 1-30, thereby delivering said non-cell penetrating peptide into said cell.

EMBODIMENTS

Embodiment 1. A nucleic acid-peptide conjugate comprising:
(i) a non-cell penetrating peptide;
(ii) a phosphorothioate nucleic acid; and
(iii) a chemical linker attaching said phosphorothioate nucleic acid to said C-terminus of said non-cell penetrating peptide;
wherein said phosphorothioate nucleic acid enhances intracellular delivery of said non-cell penetrating peptide.

Embodiment 2. The conjugate of embodiment 1, wherein said non-cell penetrating peptide is about 5, 10, 15, 20 or 25 amino acids in length.

Embodiment 3. The conjugate of one of embodiments 1-2, wherein said non-cell penetrating peptide is at least 5 amino acids in length.

Embodiment 4. The conjugate of one of embodiments 1-3, wherein said non-cell penetrating peptide is about 14 amino acids in length.

Embodiment 5. The conjugate of one of embodiments 1-4, wherein said non-cell penetrating peptide has a molecular weight of less than about 25 kD.

Embodiment 6. The conjugate of one of embodiments 1-5, wherein said non-cell penetrating peptide comprises a modified amino acid.

Embodiment 7. The conjugate of embodiment 6, wherein said modified amino acid is an alanine.

Embodiment 8. The conjugate of embodiment 7 or 8, wherein said modified amino acid is aminoisobutyric acid.

Embodiment 9. The conjugate of one of embodiments 1-8, wherein said non-cell penetrating peptide is a cyclized peptide.

Embodiment 10. The conjugate of one of embodiments 1-9, wherein said non-cell penetrating peptide comprises the sequence of SEQ ID NO:3.

Embodiment 11. The conjugate of one of embodiments 1-10, wherein said non-cell penetrating peptide is the sequence of SEQ ID NO:3.

Embodiment 12. The conjugate of one of embodiments 1-11, wherein said non-cell penetrating peptide binds an intracellular target.

Embodiment 13. The conjugate of embodiment 12, wherein said intracellular target is an oncogene.

Embodiment 14. The conjugate of embodiment 12 or 13, wherein said intracellular target is an E3 ubiquitin ligase.

Embodiment 15. The conjugate of one of embodiments 12-14, wherein said intracellular target is Hdm2.

Embodiment 16. The conjugate of one of embodiments 12-15, wherein said intracellular target is an Hdm2 protein comprising the amino acid sequence of SEQ ID NO:2.

Embodiment 17. The conjugate of one of embodiments 1-16, wherein said non-cell penetrating peptide competes with a cellular protein or cellular peptide for binding an intracellular target.

Embodiment 18. The conjugate of embodiment 17, wherein said cellular protein or cellular peptide comprises the sequence of SEQ ID NO:1.

Embodiment 19. The conjugate of embodiment 17 or 18, wherein said cellular protein or cellular peptide is a p53 protein or fragment thereof.

Embodiment 20. The conjugate of one of embodiments 1-19, wherein said phosphorothioate nucleic acid is about 10, 20, 30, 40, 50, 60, 70, 80, 90, 100 or more nucleic acid residues in length.

Embodiment 21. The conjugate of one of embodiments 1-20, wherein said phosphorothioate nucleic acid is from about 10 to about 30 nucleic acid residues in length.

Embodiment 22. The conjugate of one of embodiments 1-21, wherein said phosphorothioate nucleic acid is about 20 nucleic acid residues in length.

Embodiment 23. The conjugate of one of embodiments 1-22, wherein said phosphorothioate nucleic acid is a single stranded nucleic acid.

Embodiment 24. The conjugate of one of embodiments 1-23, wherein said phosphorothioate nucleic acid is a phosphorothioate deoxyribonucleic acid.

Embodiment 25. The conjugate of one of embodiments 1-24, wherein said chemical linker is a covalent linker.

Embodiment 26. The conjugate of one of embodiments 1-25, wherein said linker has the structure of formula:

(I)

wherein R' is hydrogen, halogen, —CF$_3$, —CN, —CCl$_3$, —COOH, —CH$_2$COOH, —CONH$_2$, —OH, —SH. —NO$_2$, —NH$_2$, —NHNH$_2$, —ONH$_2$, —NHC═(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 27. The conjugate of one of embodiments 1-26, wherein said linker is a non-immunogenic linker.

Embodiment 28. The conjugate of one of embodiments 1-26, wherein said conjugate comprises a detectable moiety.

Embodiment 29. The conjugate of embodiment 28, wherein said detectable moiety is attached to said non-cell penetrating peptide.

Embodiment 30. The conjugate of embodiment 28, wherein said detectable moiety is attached to said phosphorothioate nucleic acid.

Embodiment 31. The conjugate of any one of embodiments 1-30, bound to an intracellular target.

Embodiment 32. A cell comprising a peptide conjugate of any one of embodiments 1-30.

Embodiment 33. A pharmaceutical composition comprising a peptide conjugate of any one of embodiments 1-30 and a pharmaceutically acceptable carrier.

Embodiment 34. A method of treating cancer in a subject in need thereof, said method comprising administering to said subject a therapeutically effective amount of a cell penetrating peptide conjugate of one of embodiments 1-30, thereby treating said cancer in said subject.

Embodiment 35. The method of embodiment 34, wherein said cancer is breast cancer, prostate cancer, ovarian cancer, brain cancer, pancreatic cancer, melanoma, colon cancer, gastric cancer, head-and-neck cancer, liver cancer, lung cancer, cervical cancer, sarcoma, leukemia, lymphoma, multiple myeloma.

Embodiment 36. A method of inhibiting degradation of p53 in a cancer cell, said method comprising contacting a cancer cell with an effective amount of a cell penetrating peptide conjugate of one of embodiments 1-30, thereby inhibiting degradation of p53 in said cancer cell.

Embodiment 37. A method of inhibiting Hdm2 phosphorylation in a cell, said method comprising contacting a cell with an effective amount of a cell penetrating peptide conjugate of one of embodiments 1-30, thereby inhibiting Hdm2 phosphorylation in said cell.

Embodiment 38. A method of delivering a non-cell penetrating peptide into a cell, said method comprising contacting a cell with a cell penetrating peptide conjugate of any one of embodiments 1-30, thereby delivering said non-cell penetrating peptide into cell.

What is claimed is:

1. A nucleic acid-peptide conjugate comprising:
   (i) a non-cell penetrating peptide;
   (ii) a phosphorothioate nucleic acid; and
   (iii) a chemical linker attaching said phosphorothioate nucleic acid to the C-terminus of said non-cell penetrating peptide;
   wherein said phosphorothioate nucleic acid enhances intracellular delivery of said non-cell penetrating peptide and wherein said non-cell penetrating peptide comprises the sequence of SEQ ID NO:3.

2. The conjugate of claim 1, wherein said non-cell penetrating peptide binds an intracellular target.

3. The conjugate of claim 2, wherein said intracellular target is Hdm2.

4. The conjugate of claim 2, wherein said intracellular target is an Hdm2 protein comprising the amino acid sequence of SEQ ID NO:2.

5. The conjugate of claim 1, wherein said phosphorothioate nucleic acid is about 10, 20, 30, 40, 50, 60, 70, 80, 90, 100 or more nucleic acid residues in length.

6. The conjugate of claim 1, wherein said phosphorothioate nucleic acid is about 20 nucleic acid residues in length.

7. The conjugate of claim 1, wherein said phosphorothioate nucleic acid is a single stranded nucleic acid.

8. The conjugate of claim 1, wherein said chemical linker is a covalent linker.

9. The conjugate of claim 1, wherein said conjugate comprises a detectable moiety.

10. The conjugate of claim 1, bound to an intracellular target.

11. A pharmaceutical composition comprising the peptide conjugate of claim 1 and a pharmaceutically acceptable carrier.

* * * * *